(12) United States Patent
Gage

(10) Patent No.: US 9,289,462 B2
(45) Date of Patent: Mar. 22, 2016

(54) METHOD FOR MEDICAL TREATMENT UTILIZING GLUTATHIONE

(76) Inventor: Terry Gage, St. Lubbock, TX (US)

( * ) Notice: Subject to any disclaimer, the term of this patent is extended or adjusted under 35 U.S.C. 154(b) by 1839 days.

(21) Appl. No.: 12/232,434

(22) Filed: Sep. 17, 2008

(65) Prior Publication Data

US 2010/0069309 A1 Mar. 18, 2010

(51) Int. Cl.
*A61K 38/06* (2006.01)

(52) U.S. Cl.
CPC .................................. *A61K 38/063* (2013.01)

(58) Field of Classification Search
None
See application file for complete search history.

(56) References Cited

PUBLICATIONS

Neuschwander-Tetri et al. "Glutathione Monoethyl Ester Ameliorates Caerulein-induced Pancreatitis in the Mouse." Journal Clin. Invest. vol. 89, pp. 109-116. Jan. 1992.*

Grattagliano et al. "Disposition of Glutathione Monoethyl Ester in the Rat: Glutathione Ester is a Slow Release Form of Extracellular Glutathione." The Journal of Pharmacology ian Experimental Therapeutics, vol. 272, No. 2. pp. 484-488. 1995.*

File HCAPLUS on STN. DN No. 145:459178. Huang et al. "Protective effect of reduced glutathione on multiple organ function in patient with acute pancreatitis." Zhongguo Weizhongbin Jijiu Yixue (2005), 17(11), 673-674. Abstract Only. Date of Abstract: Jan. 23, 2006.*

"Glutathione, Reduced (GSH)." Alternative Medicine Review. vol. 6, No. 6, pp. 601-607. 2001.*

Cacciatore, et al., "Prodrug Approach for Increasing Cellular Glutathione Levels." Molecules, 15, 1242-1264 (2010).*

G.D. Zeevalk, et al., "Characterization of intracellular elevation of glutathione (GSH) with glutathione monoethyl ester and GSH in brain and neuronal cultures: Relevance to Parkinson's disease." Experimental Neurology, 203, 518 (2007).*

Siriwardena et al. "Randomised, double blind, placebo controlled trial of intravenous antioxidant (n-acetylcysteine, selenium, vitamin C) therapy in severe acute pancreatitis." Gut, vol. 56, pp. 1439-1444. 2007.*

Australian Office Action dated Apr. 14, 2015, in connection with AU Application No. 2009293612.

* cited by examiner

*Primary Examiner* — Christina Bradley
(74) *Attorney, Agent, or Firm* — Maier & Maier, PLLC

(57) ABSTRACT

A method of treating a condition or conditions caused by damage to cells by a process of oxidative stress and glutathione depletion. In some exemplary embodiments, the condition or conditions may be treated by administering reduced L-glutathione to a patient through injection or intravenous infusion. In other exemplary embodiments, the condition or conditions may be treated by administering reduced glutathione monoethyl ester through injection or intravenous infusion.

3 Claims, No Drawings

METHOD FOR MEDICAL TREATMENT UTILIZING GLUTATHIONE

BACKGROUND

Glutathione, a tripeptide molecule, occurs naturally in mammalian cells and is an important antioxidant. The reduced form of glutathione, GSH, readily donates a reducing equivalent to unstable molecules, and is thus vital to combating oxidative stress in cells and the cell death that is a consequence of such stress. Upon donation of a reducing equivalent, GSH becomes reactive and binds with another reactive GSH to form glutathione disulfide (GSSG), which is then converted to GSH by the enzyme glutathione reductase.

Healthy cells generally maintain a 9:1 GSH to GSSG ratio. A decrease in the ratio of GSH to GSSH is indicative of oxidative stress. Oxidative stress may result in cell death and is involved in the pathophysiologic processes of many diseases, including pancreatitis.

Pancreatitis is an inflammatory condition of the pancreas that is painful and may be fatal. The mortality rate for acute pancreatitis has remained at about 10% despite medical advances, while the mortality rate for chronic pancreatitis is estimated at 70-80% within 10 years of diagnosis. It is known that GSH depletion as a result of xenobiotic or oxidative stress plays a significant role in the development of pancreatitis.

Previous methods of treating pancreatitis using glutathione precursors have been unsuccessful and, in some cases, detrimental to patients. For example, one study, found at http://gut.bmj.com/cgi/content/full/56/10/1439, which is hereby incorporated by reference in its entirety, found no therapeutic response when treating subjects with glutathione precursors and, in fact, found a slightly worse outcome in their conditions.

SUMMARY

In an exemplary embodiment, a method of treatment of diseases, conditions, afflictions and symptoms through the administration of glutathione may be disclosed.

In another exemplary embodiment, a method of medical treatment utilizing reduced L-glutathione and reduced glutathione ester may be disclosed.

In another exemplary embodiment, a method of medical treatment utilizing reduced L-glutathione may be disclosed.

In another exemplary embodiment, a method of medical treatment utilizing reduced glutathione ester may be disclosed.

In still another exemplary embodiment, a method of treating a condition caused by damage to cells by a process of oxidative stress and glutathione depletion may be disclosed. The treatment may be performed by administering at least one of reduced L-glutathione and reduced glutathione monoethyl ester through one of intravenous infusion or injection.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

It has been found that glutathione and glutathione esters act as prophylactic and therapeutic agents against a wide variety of ailments. Previous studies have shown that improving depleted glutathione concentrations may potentially have beneficial effects in the treatments of influenza, tuberculosis, retroviral infections including HIV, rhinoviral infections, spinal cord injuries, and pulmonary diseases.

Studies have also shown that glutathione depletion plays a significant role in the development of many afflictions, conditions and diseases, for example acute and chronic pancreatitis. Pancreatitis may be any of a variety of afflictions, such as chronic pancreatitis, intermittent recurrent pancreatitis, acute pancreatitis and/or fulminate acute hemorrhagic pancreatitis. In the evolution of, for example, chronic pancreatitis, glutathione depletion may occur as a result of xenobiotic stress. In acute pancreatitis, glutathione depletion may occur as a result of stress from reactive oxygen species. It was also found that heightened oxidative stress characterized by glutathione depletion may be of importance in mediating the progression from mild to severe pancreatitis.

An inflamed pancreas may not be capable of synthesizing adequate glutathione from precursors, such as n-acetylcysteine. Consequently, the administration of glutathione precursor n-acetylcysteine and the antioxidants selenium and vitamin C failed to show any benefit in studies on patients with acute pancreatitis. However, the administration of glutathione was shown to have a protective effect on multiple organ functions in patients with acute pancreatitis.

In one exemplary embodiment, a tripeptide or group of three amino acids, for example a solution of pharmaceutical grade reduced L-glutathione and reduced glutathione monoethyl ester may be prepared. In other exemplary embodiments, L-glutathione may be referred to as GSH, N-L-gamma-glutamyl-cysteinyl glycine, 2-amino-4-[[1-(carboxymethylcarbamoyl)-2-sulfanyl-ethyl]carbamoyl] butanoic acid and/or $C_{10}H_{17}N_3O_6S$. The ratios of reduced L-glutathione to reduced glutathione monoethyl ester may vary from a 10:1 to 1:10, for example a 1:1 ratio of reduced L-glutathione to reduced glutathione monoethyl ester. Reduced glutathione monoethyl ester may be readily transported into various cells, may not be readily taken up by the liver and may therefore be more effective than reduced L-glutathione in raising intracellular glutathione levels in cells that possess functional esterase enzymes to hydrolyze the ester form into reduced L-glutathione. Reduced L-glutathione, which may be less efficiently taken up by cells, can already be in the active form and thus functional esterase enzymes are not necessary. A mixture of reduced L-glutathione and reduced glutathione monoethyl ester therefore may incorporate the strengths of both molecules in the treatment process.

The following examples are offered by way of illustration and not by way of limitation.

EXAMPLE 1

A 64 year old male patient who has experienced over 5 years of constant abdominal pain secondary to chronic pancreatitis is given intravenous reduced L-glutathione therapy.

The patient had previously been treated with hydrocodone and fentanyl patch, and also considered the possibility of celiac nerve block. Within four months of initiating reduced L-glutathione therapy, the patient reports an absence of pain, as shown in Table 1 below. The patient elects to continue a monthly reduced L-glutathione infusion for maintenance and is without pain.

TABLE 1

| Dates of GSH (1 gm) IV | Pain Score | Pain Medications |
|---|---|---|
| Sep. 28, 2007 | 8 of 10 | hydrocodone |
| Oct. 10, 2007 | 5 of 10 | propoxyphene |
| Oct. 29, 2007 | 2 of 10 | propoxyphene |
| Nov. 12, 2007 | 1 of 10 | propoxyphene |
| Dec. 10, 2007 | 1 of 10 | propoxyphene |
| Dec. 17, 2007 | 0 of 10 | None |
| Jan. 3, 2008 | 0 of 10 | None |

As shown in Table 2 below, the patient's amylase and lipase levels were also significantly reduced during the course of treatment.

TABLE 2

| Dates | Amylase | Lipase |
|---|---|---|
| Normal | 30-110 | 8-57 |
| Sep. 14, 2007 | 90 | 108 |
| Sep. 28, 2007 | 79 | 64 |
| Nov. 5, 2007 | 62 | 39 |
| Jun. 27, 2008 | 68 | 30 |

EXAMPLE 2

A 48 year old male developed acute pancreatitis after initiating exenatide injection therapy for diabetes. On Feb. 7, 2008, the patient's amylase and lipase levels were 114 and 128, respectively. The patient improved substantially over a several week period on nonspecific supportive therapy but continued to require pain medication intermittently. The patient reported on May 7, 2008 that he was enduring increasing abdominal pain over ten day's duration. The patient's pain was described as 10/10, but was relieved to 5/10 with the hydrocodone he was taking at home. The patient's pain and enzyme levels responded to a single dose of intravenous reduced L-glutathione and his amylase and lipase levels decreased, as shown in Table 3 and Table 4 below, respectively.

TABLE 3

| Dates of GSH (1 gm) IV | Pain Score | Pain Medications |
|---|---|---|
| May 7, 2008 | 5 of 10 | hydrocodone |
| *May 9, 2008 | 0 of 10 | None |

*Follow up visit only, no infusion given. Patient has not returned for further follow up.

TABLE 4

| Dates | Amylase | Lipase |
|---|---|---|
| Normal | 30-110 | 8-57 |
| May 7, 2008 | 115 | 161 |
| May 9, 2008 | 105 | 132 |

EXAMPLE 3

A 69 year old male had experienced 5 weeks of increasing back and abdominal pain prior to first dose of intravenous L-glutathione. Numerous CT scans and thoracic spine MRIs were unrevealing. Two epidural steroid injections were unsuccessful in pain relief. The patient's only abnormal studies were increased pancreatic enzymes. The patient elected to undergo intravenous L-glutathione reduced therapy for pancreatitis. Within a month, the patient showed a significant decrease in pain, as seen in Table 5, as well as a reduction in amylase, lipase and C-reactive protein levels, as seen in Table 6.

TABLE 5

| Dates of GSH (1 gm) | Pain Score | Pain Medications |
|---|---|---|
| Jun. 3, 2008 | 5 of 10 | hydrocodone |
| Jun. 4, 2008 | 0 of 10 | hydrocodone |
| Jun. 5, 2008 | 2.5 of 10 | hydrocodone |
| Jun. 6, 2008 | 4.5 of 10 | hydrocodone |
| Jun. 9, 2008 | 3 of 10 | hydrocodone |
| Jun. 16, 2008 | 0 of 10 | None |
| Jun. 18, 2008 | 0 of 10 | None |
| Jun. 25, 2008 | 2 of 10 | Back pain due to lifting furniture |

TABLE 6

| Dates | Amylase | Lipase | CRP |
|---|---|---|---|
| Normal | 30-110 | 8-57 | 0-7.48 |
| May 22, 2008 | 105 | 150 | |
| May 30, 2008 | 124 | 150 | |
| Jun. 3, 2008 | 95 | 112 | 7.84 |
| Jun. 5, 2008 | 128 | 152 | 9.11 |
| Jun. 16, 2008 | 75 | 89 | |
| Jun. 25, 2008 | 64 | 60 | 3.97 |

In further exemplary embodiments, a dosage for injection or intravenous infusion of L-glutathione reduced with, or without, mixture with various glutathione esters, for example diethyl ester or isopropyl ester, may range from 800 mg to 3 grams in a single dose or over multiple dosings in a day. For example, a typical dose may be 1 to 2 grams once daily or at any other varied time interval, depending on the specific indications and severity of the disease or condition being treated. Also, one mixture of L-glutathione reduced mixed with glutathione esters reduced of various type may range from a 10:1 ratio to a 1:10 ratio, for example a 1:1 ratio using a glutathione monethyl ester. Additionally, L-glutathione and glutathione ester reduced may be considered to be of low toxicity. Therefore, for example, a 3 gram dose administered to a human of 70 kg would be a dose of 0.043 g/kg, which would provide a wide therapeutic index given a known toxicity LD 50 value of about 5.3 g/kg in the case of glutathione isopropyl ester.

In another exemplary embodiment, a method of treatment of various conditions and diseases may be described. For example, pharmaceutical grade L-glutathione reduced or an about 1:1 mixture of L-glutathione reduced and glutathione monoethyl ester reduced may be prepared according to known pharmaceutical standards and processed into a fluid solution for intravenous infusion or injection. Dosage may be varied depending on individual patients and conditions, but may have a concentration of about 100 mg/ml in a single-dose, 10 ml vial, yielding a total dose of about 1 gram. This dose may be further diluted at the time of administration with about 10 ml NS to a total volume of about 20 ml, which may be infused intravenously over about a 20 minute interval. However, other exemplary embodiments may include different dosage amounts, ratios and/or infusion rates. Further, the method may be adjusted depending on need or characteristics of an individual patient.

In another exemplary embodiment of a method of treating pancreatitis, L-glutathione reduced may be mixed with an about 1:1 ratio of glutathione monoethyl ester reduced, and the mixture may be administered intravenously. Here, the glutathione monoethyl ester reduced may be especially effective in raising intracellular glutathione levels, for example, if the cell is well enough to have the functional esterase enzymes needed to hydrolyze the ester form into an active form GSH or L-glutathione reduced. Further, L-glutathione may be in its active form and capable of ameliorating the disease process without any form of conversion. Therefore, the strengths of glutathione monoethyl ester reduced and L-glutathione reduced may be emphasized in such a mixture.

In additional exemplary embodiments, reduced L-glutathione and reduced glutathione monoethyl ester may be used to treat, reduce the occurrence of or prevent any of a variety of other diseases, conditions or ailments. For example, the reduced L-glutathione and reduced glutathione monoethyl ester may be used to treat, reduce the occurrence of any of a variety of conditions that may be associated with pancreatitis or that may lead to pancreatitis. Such conditions may include, but are not limited to, gallstones, choledocholithiasis, postoperative complications of endoscopic retrograde choloangiopancreatography, surgery on the gall bladder, pancreas or adjacent organs, alcoholism, hypertrigliceridemia, intraabdominal infection, viral infection, sepsis, septic shock, idiopathic pancreatitis, vasculitis, blunt traumatic injury, congenital pancreas divisum, porphyrias and immune rejection of the transplanted pancreas.

In still further exemplary embodiments, reduced L-glutathione and reduced glutathione monoethyl ester may be used to treat, reduce the occurrence of or prevent other states leading to oxidative stress on the pancreas and glutathione depletion from toxins, ethanol abuse, xenotoxins, intraabdominal infection, malignancy, radiation therapy, autoimmune disorders and other multiple causes of oxidative stress of the pancreas. Further, the compositions may be used to reduce the occurrence of or prevent major events of pancreatitis and potentially prevent death in patients who are at risk of increasing pancreatic inflammation. Also, the compositions of reduced L-glutathione and reduced glutathione monoethyl ester may also be used in the treatment and reduction of markers of pancreatic inflammation, such as amylase, lipase, C reactive protein and others with resultant beneficial therapy causing reduction of these markers of pancreatic inflammation and amelioration of pain, hemorrhage, poor nutritional intake and any of a variety of other effects of pancreatitis in any of its forms.

Still other diseases and conditions pathophysiologically related to oxidative stress and glutathione deficiency may be treated using the methodology described herein. For example, pancreatitis in any form, Neurologic disease exacerbated by oxidative stress, Parkinson's disease, Alzheimer's disease, Multiple Sclerosis, Autism, Cystic fibrosis, various forms of Hepatitis, Rhinovirus (and other viral illnesses of the upper and/or lower respiratory tract), amyotrophic lateral sclerosis, stroke, cerebrovascular accident, myocardial infarction, cardiac failure, congestive heart failure, diseases of coronary endothelial vasomotor dysfunction, sepsis, septic shock, wound healing complications, bacterial pneumonia, viral pneumonia, COPD and other lung conditions, oxygen toxicity in premature infants, radiation toxicity and oxidative stress and cell damage resulting from ischemia to heart, brain or spinal cord tissue, as well as various infections and immuno-deficiency conditions, may be treated through the use of reduced L-glutathione and reduced glutathione monoethyl ester as described herein. Other conditions, such acetaminophen overdose, HIV/AIDS and GSH deficiency related maladies associated with HIV/AIDS, inflammatory bowel, colon and small intestine diseases of all types, avian influenza, hanta virus, other types of influenza, cirrhosis and other inflammatory states of the liver, acute respiratory distress syndrome, cataracts, macular degeneration of the eye, major trauma, spinal cord injury and other injuries to the central nervous system, burns, amelioration of the side effects of chemotherapy and radiation therapy of cancer treatment, heavy metal toxicity, organic poison toxicity, glucose-6-phosphate dehydrogenase (g6pd) deficiency, chronic fatigue syndrome, pulmonary fibrosis, chronic obstructive pulmonary disease, various dermatologic conditions, such as acne, eczema, psoriasis, darkening of skin and wrinkle formation may also be treated through the use of reduced L-glutathione and reduced glutathione monoethyl ester. Also, reduced L-glutathione and reduced glutathione monoethyl ester may be used in the prevention and treatment of ischemic and reperfusion injuries related to transplant surgery of all types, coronary artery bypass grafting, angioplasty and vascular surgery, for example.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method of treating a condition caused by damage to cells by a process of oxidative stress and glutathione depletion, comprising:
    administering a mixture of reduced L-glutathione and reduced glutathione monoethyl ester through one of intravenous infusion or injection, wherein the ratio of reduced L-glutathione to glutathione monoethyl ester is within the range of 10:1 to 1:10, and wherein the condition is pancreatitis.

2. The method of claim 1, wherein the reduced L-glutathione is of the formula $C_{10}H_{17}N_3O_6S$.

3. The method of claim 1, wherein the reduced glutathione monoethyl ester is of the formula $C_{12}H_{21}N_3O_6S$.

* * * * *